United States Patent
Kuhns

(10) Patent No.: US 7,392,762 B2
(45) Date of Patent: Jul. 1, 2008

(54) METHOD FOR SITE-SPECIFIC APPLICATION OF TOPICAL MEDICANTS TO AQUATIC ANIMALS

(75) Inventor: John Farrell Kuhns, Parkville, MO (US)

(73) Assignee: Aquscience Research Group, Inc., North Kansas, MO (US)

( * ) Notice: Subject to any disclaimer, the term of this patent is extended or adjusted under 35 U.S.C. 154(b) by 0 days.

(21) Appl. No.: 11/774,629

(22) Filed: Jul. 9, 2007

(65) Prior Publication Data

US 2007/0254018 A1    Nov. 1, 2007

Related U.S. Application Data

(62) Division of application No. 10/899,614, filed on Jul. 27, 2004.

(51) Int. Cl.
*A01K 39/00* (2006.01)
(52) U.S. Cl. ................................. 119/231; 424/184.1
(58) Field of Classification Search .............. 119/231, 119/215; 424/725, 184.1
See application file for complete search history.

(56) References Cited

U.S. PATENT DOCUMENTS

| | | | |
|---|---|---|---|
| 4,110,467 A | 8/1978 | Sano et al. | |
| 4,826,842 A * | 5/1989 | Mehlhorn et al. | 514/241 |
| 4,844,898 A | 7/1989 | Komori et al. | |
| 4,852,519 A | 8/1989 | Karlsen | |
| 5,188,832 A * | 2/1993 | Mehlhorn et al. | 424/405 |
| 5,411,945 A | 5/1995 | Ozaki et al. | |
| 5,518,902 A | 5/1996 | Ozaki et al. | |
| 5,618,799 A | 4/1997 | Inagi et al. | |
| 5,722,942 A | 3/1998 | Tanaka et al. | |
| 6,054,454 A | 4/2000 | Schmid et al. | |
| 6,160,023 A * | 12/2000 | Braidwood | 514/727 |
| 6,329,343 B1 | 12/2001 | Leung et al. | |
| 6,366,145 B1 * | 4/2002 | Williams et al. | 119/215 |
| 6,518,252 B2 | 2/2003 | Wooley et al. | |
| 6,596,298 B2 | 7/2003 | Leung et al. | |
| 7,029,586 B2 * | 4/2006 | Austin et al. | 210/602 |
| 2007/0244199 A1 * | 10/2007 | Parrish et al. | 514/625 |

* cited by examiner

*Primary Examiner*—Yvonne R Abbott

(57) ABSTRACT

Method for site-specific application of a topical medicant for fishes, amphibians, reptiles, and aquatic macroinvertebrates applied in a site-specific manner for the localized treatment of skin wounds, lesions and diseases. The medicant comprises a hydrophilic carrier with an antimicrobial therapeutant formulated as a water-soluble resistant, hydrated gel or dry powder that hydrates and gels on contact with a moistened integument area.

13 Claims, No Drawings

METHOD FOR SITE-SPECIFIC APPLICATION OF TOPICAL MEDICANTS TO AQUATIC ANIMALS

CROSS-REFERENCE TO RELATED APPLICATIONS

This application is a divisional application of copending nonprovisional application Ser. No. 10/899,614, filed Jul. 27, 2004.

STATEMENT REGARDING FEDERALLY SPONSORED RESEARCH OR DEVELOPMENT

Not applicable.

BACKGROUND OF THE INVENTION

This invention relates to the direct topical medication of fishes, amphibians, reptiles, and aquatic macroinvertebrates. More specifically, this invention relates to topical medicants for individual such aquatic and semi-aquatic animals applied in a site-specific manner for the localized treatment of skin wounds, lesions and diseases.

In the animal health care field, there have been many advances in the veterinary sciences for the disease treatment of mammals as a result of the important roles of livestock and pets in our society. Historically, the same emphasis has not been placed on the care and treatment of diseased cold-blooded life forms. As the economic impact of aquaculture practices such as fish farming grows, as well as sophistication of commercial, public and hobby aquarium and terrarium maintenance, greater attention is being given to the medical needs of fishes, amphibians, reptiles, and aquatic macroinvertebrates.

Traditional methods for treating fishes involve administering a therapeutic agent orally with feed, parenterally by injection, or by dispersing in a water bath or dip. By far the most frequently used treatment method involves medicating the water in which the fish lives. U.S. Pat. No. 4,110,467 to Sano et al. and U.S. Pat. No. 4,852,519 to Karlsen are examples of the state of the art techniques for medicating water in order to treat fishes.

The well-known problems of "fin and tail rot", "mouth fungus", cataracts of the eyes, as well as wounds and lesions, are treated with therapeutic topical baths of indeterminate length or short-term dips. In all of these examples, there are either no known treatments, or treatments which have not always been effective due to the inability to get sufficient therapeutants to the site of active disease, or due to loss of the therapeutants in the bath as a result of decomposition or adsorption onto gravel, rocks and other decorations and implements in the environment, as well as removal by filtration.

Mass treatments in the form of baths and dips suffer a variety of drawbacks. Such technique is likely to waste therapeutants, to expose non-diseased animals to the treatment, and to potentially destroy non-target microbes such as the nitrifying bacteria in aquarium or pond biological filtration. The inability to accurately calculate the exact volume of water being treated in an aquarium or pond typically leads to undesirable under-dosing or over-dosing of the treatment. In addition, there is the danger of creating resistant strains of disease-causing organisms by exposing other than the target organisms to otherwise effective therapeutants. And, although useful against the target organisms, therapeutants in a water bath or dip may be toxic to the animals being treated.

Apart from limited use of the topical bath/dip treatments for diseases of fishes, reptiles and amphibians, treatments for aquatic macroinvertebrates are less well known. Macroinvertebrates include crustaceans, mollusks, corals, echinoderms such as sea cucumbers and sea stars. For example, a major problem in the husbandry of brittle sea stars (i.e., starfish) is the loss of the animal's arms during shipping or handling. Such an injury can easily result in the loss of internal fluids and the invasion of disease-causing microbes. Similarly, bacterial infections of stony corals cause widening spots or bands to appear on the coral heads or extensions. Topical treatment by bath medication for such wounds and diseases has not proven efficacious.

As used in this disclosure, the term "topical" refers to any substance, compound or mixture that is applied directly to the integument (e.g., skin) of invertebrate and vertebrate animals. Such application may consist of direct deposition on the integument by means of swabbing, spraying, bathing, plastering, or rubbing.

For various reasons, each application method has identifiable drawbacks. For instance, in fishes, amphibians and aquatic macroinvertebrates, the application of topical treatments is most often in the form of a bath where the animal is immersed in the medicated water for periods of a few seconds to a week or more. The obvious problems associated with baths are: (1) the difficulty of accurately calculating dosages in oddly shaped bodies of water; (2) the reaction of the dissolved or dispersed medication with other substances in the water; (3) the removal of the medication by filtration or by simple adsorption on container walls or substrates; (4) the inability to readily determine the efficacy of the treatment; (5) the exposure of otherwise healthy animals to a treatment that may only be needed for a single specimen; (6) the inability to easily determine the concentrations of therapeutants in baths and dips; and (7) the exposure of a mixed species population to a treatment that may be toxic, or otherwise detrimental, to some of the species in the culture water.

Topical medicants applied as ointments and salves have been primarily made for veterinary use. In nearly every instance these have been oil or petroleum jelly based products, which do not adhere well to the wetted skin of fishes. In those exceptional instances where these products are water based, the viscosity is such that they do not remain on the area to which they are applied, and they lack properties that allow them to adhere to the area of application without quickly washing off into the surrounding water.

Plastering, daubing, rubbing, swabbing and spraying are the typical application methods of topical treatments for semi-aquatic animals. For instance, antimicrobial ointments are routinely used to treat lesions and wounds on herpatiles (i.e., reptiles and amphibians). Such ointments are typically swabbed using sterile cotton-tipped applicators, daubed directly from the container, plastered using plastic, metal or wooden applicators, or rubbed onto the site needing treatment with a properly gloved hand or finger. In such applications, the wounds or lesions are usually debrided to remove dead and decaying tissue and contaminates. Among the drawbacks to such applications are the necessity to capture and restrain the animal being treated, the possibility of exacerbating the severity of the lesions or wounds during capture and restraint, and the necessity of direct contact with an application instrument to properly apply the ointment.

Sprays suffer from the problem of dispersing the medication in a liquid form that will easily pass through an applicator orifice without clogging. In addition, sprays will typically cause the medication to be applied to a wider than necessary area of the animal's integument or immediate environment, thus wasting the medication. Treatments that are of a low enough viscosity to pass easily through a spray nozzle will typically run off vertical surfaces and may not provide sufficient coverage of the area to be treated. Another concern is that the sound, odor or temperature of sprays may startle or frighten the animal being treated.

The application of powders through dusters or direct application with a utensil suffers essentially the same drawbacks of liquid sprays and of ointments. With powders, there are the additional concerns of the powder not readily adhering to the lesion or wound being treated and being quickly shed or dispersed into the treated animals' environments. In the case of aquatic and semi-aquatic animals, powdered medications are practically useless for the foregoing reasons. For animals such as lizards, snakes, tortoises and toads, the animal crawling through water in its environment makes the use of powdered medications difficult and ineffective in most circumstances.

Accordingly, there remains a need in the animal health care field for therapeutic formulations and reliable methods of applying such formulations to fishes, amphibians, reptiles, and aquatic macroinvertebrates. The primary objective of this invention is to meet this need.

BRIEF SUMMARY OF THE INVENTION

More specifically, an object of this invention is to provide a topical medicant for fishes, amphibians, reptiles, and aquatic macroinvertebrates applied in a site-specific manner for the localized treatment of skin wounds, lesions and diseases.

Another object of the invention is to provide a topical medicant of the character described so that a single animal can be treated within a community population without exposure of the entire population to the treatment.

An additional object of the invention is to provide a topical medicant of the character described which may be formulated from known antimicrobial therapeutants combined with a hydrophilic carrier to cause the medicant to substantially remain in contact with a treated integument region of the animal even when living in aquatic environs.

A corollary object of the invention is to provide a topical medicant of the character described formulated from antimicrobial therapeutants, which would otherwise be too expensive for use with traditional bath or dip treatments.

A further object of the invention is to provide a topical medicant of the character described formulated from antimicrobial therapeutants in preselected amounts known to be effective for the condition to be treated.

Another object of the invention is to provide a topical medicant of the character described which remains visible on the integument region of a treated animal as an indication of medical treatment. This feature aids in follow-up care for determining when re-application of the medicant may be necessary.

Yet another object of the invention is to provide a topical medicant of the character described formulated as a hydrated gel or as a dry powder that hydrates and gels upon contact with a moistened integument region.

An alternative object of this invention is to provide a method for applying a topical medicant having the foregoing characteristics for fishes, amphibians, reptiles, and aquatic macroinvertebrates in a quick and easy manner to a specific integument region for the localized treatment of skin wounds, lesions and diseases.

A further object of the invention is to provide a method of the character described which minimizes the handling of the animal to be treated.

Another object of the invention is to provide a method of the character described wherein the topical medicant may be applied as a hydrated gel dispensed from an applicator or as a hydratable powder puffed onto a moistened integument region so that little or no contact with the area being treated is necessary.

An additional object of the invention is to provide a method of the character described wherein the topical medicant may be applied directly to a wound site as a packet of hydratable powder within a porous or water-soluble bag.

Other and further objects of the invention, together with the features of novelty appurtenant thereto, will appear in the detailed description of the invention.

In summary, an object of the invention is to provide a topical medicant for fishes, amphibians, reptiles, and aquatic macroinvertebrates applied in a site-specific manner for the localized treatment of skin wounds, lesions and diseases. The medicant comprises a hydrophilic carrier with an antimicrobial therapeutant formulated as a water-soluble resistant, hydrated gel or dry powder that hydrates and gels on contact with a moistened integument area.

DETAILED DESCRIPTION OF THE INVENTION

It has been discovered that a specially formulated topical medicant can be applied to specific integument areas of fishes, amphibians, reptiles, and aquatic macroinvertebrates for the localized treatment of skin wounds, lesions and diseases. The topical medicant comprises a hydrophilic carrier and an antimicrobial therapeutant formulated either as a hydrated gel or as a hydratable dry powder. The therapeutant may be any known agent having medicinal properties. Known adjuncts with special animal health care characteristics may also be combined in the topical medicant.

In both the gel and powder forms, the hydrophilic carrier useful in the present invention includes synthetic and natural polymers, resins, gums and colloids. More specifically, polyvinyl-containing polymers, alginic acid derivatives, acrylic polymers, cellulosic polymers, carrageenan derived colloids, and plant and animal source gums, as well as mixtures of these components, will serve as an effective hydrophilic carrier in the topical medicant. The polyvinyl-containing polymers may be either nonionic or anionic and either cross-linked or non-cross linked. Examples of vinyl-containing gums and resins include Polyvinylpyrrolidone and Polyvinylalcohol. Polymeric glycols such as Polyethyleneglycol may also be used. The alginic acid derivatives (i.e., alginates) may be either nonionic or anionic. Likewise, the acrylic and cellulosic polymers may be either nonionic or anionic. The acrylic-containing gums and resins include, for example, polyacrylamide. Cellulose gums include hydrocolloidal polysaccharides such as Carboxymethylcellulose and its salts (usually sodium), Microcrystalline cellulose, Methylcellulose, Hydroxypropylmethylcellulose, Hydroxyethylcellulose, Ethylhydroxyethylcellulose and other alkylhydroxyalkylcellulose gums. Plant and animal source gums include Agar-agar, Arabic, Alginate, Carrageen, Gelatin, Guar, Karaya, Locust bean, Pectin, Tragacanth, Psyllium seed, Starches such as tapioca, sago and arrowroot, Larch, Quince seed, Furcellaran, and Ghatti. There are also suitable gums made by yeast and other microorganisms, these include Gellan gum, Pullulan, and Curdlan.

In preferred embodiments of the invention, therefore, the hydrophilic carrier will most likely be selected from the group consisting of Polyvinylpyrrolidone, Polyvinylalcohol, Polyethyleneglycol, Alginic Acid Derivatives, Polyacrylamide, Carboxymethylcellulose, Sodium Carboxymethylcellulose, Microcrystalline Cellulose, Methylcellulose, Hydroxypropylmethylcellulose, Hydroxyethylcellulose, Ethylhydroxyethylcellulose, Agar-agar, Arabic, Alginate, Carrageen, Gelatin, Guar, Karaya, Locust Bean, Pectin, Tragacanth, Psyllium Seed, Tapioca Starch, Sago Starch, Arrowroot Starch, Larch, Quince Seed, Furcellaran, Ghatti, Gellan Gum, Pullulan, and Curdlan.

In general, for hydrated gel formulations, the polymers, resins, gums, and colloids, which form the hydrophilic carrier in the mixture, may be adjusted as needed to achieve two basic objectives. First, it is desirable that the hydrated gel be dispensed from a squeeze bottle or tube container without touching any part of the container to the animal being treated. In other words, the viscosity of the hydrated gel is not such that any additional implement is needed to remove the gel from its container or to apply it to the target area. Second, the hydrated gel must be viscous enough to stay on the integument area of application without running off. Typical hydrated gel formulations, therefore, will have a concentration of polymers, resins, gums, and colloids at a concentration falling in the range of 4% to 16% by weight. The minimum viscosity should be approximately equivalent to about a 5% aqueous solution of Povidone with an average molecular weight of 58,000. Viscosity of the hydrated gel will preferably fall in the range of 2.5 to 40 millipascal-seconds.

In dry formulations, the amount of polymers, resins, gums and colloids which form the hydrophilic carrier needs to be small enough so that rapid hydration occurs upon contact with the wet or moist integument area to which it is applied, and great enough to remain in contact with the integument area to which it is applied after hydration. Additionally, the ratio of the weight of the hydrophilic carrier to that of the therapeutants must be such that the therapeutants, if water-soluble, will not readily dissolve from the hydrated gel matrix. In other words, it is important that of the therapeutants be permitted to migrate through the gel to the site of the wound. To meet these requirements, the polymers, resins, gums and colloids must be present in the dry mixture at a weight-weight percentage equivalent to no less than a 2% aqueous solution of Povidone having an average molecular weight of 58,000. Moreover, the physical form of the polymers, resins, gums and colloids must be that of a powder finer than 100 mesh to prevent formation of partially hydrated clumps once the dry formulation is wetted. The maximum amount of the polymers, resins, gums and colloids in the dry mixture should be equivalent to no more than 32% by weight.

The hydrophilic carrier should have an additional, important characteristic. It should resist water solubility. This applies both the hydrated gel and also to the dry powder formulation after hydration to a gel. It is this quality of the topical medicant that enables the therapeutant to remain active at the site of the wound, lesion or disease being treated. The hydrophilic carrier is not, however, waterproof. Over time, the gel will eventually swell with absorbed water and dissolve away. The more active the animal is to which the medicant has been applied, the faster the dissipation of the gel and this, in turn, may require more frequent re-application of the medicant.

As used in this disclosure, the term "antimicrobial" encompasses antibacterials, antifungals, antiprotozoals and antivirals. Antimicrobial therapeutants useful in this invention may include any one or more of the general groups of bactericides, bacteriostats, disinfectants, medicinal dyes, topical antiseptics, therapeutic metal salts, antiparasiticals, and antifungal agents. More specifically, the antimicrobial therapeutant may be selected from the group consisting of 8-Quinolinol, Acriflavine, Amoxacillin, Bistriazole, Bronopol, Chloramphenicol, Chloroquin, Cinnamon Leaf Oil, Clove Oil, Copper Salts, Eugenol, Flubendazole, Furazolidone, Gentamycin, Gentian Violet, Griesofulvin, Imidazole, Iodine, Iron Salts, Kanamycin, Macrolides, Malachite Green, Melaleuca, Merbromin, Merthiolate, Methylene Blue, Metronidazole, Miconazole, Naladixic Acid, Neomycin, Nifurpirinol, Nitrofurazone, Norfloxacin, Oxacillin, Oxolinic Acid, Oxytetracycline, Phenoxyethanol, Povidone-Iodine, Praziquantel, Quaternary Ammonium Compounds, Quinine, Quinolines, Streptomycin, Sulfisoxazole, Tetracycline, Tolnaftate, Trimethroprin, and mixtures thereof.

In hydrated gel formulations, as well as the hydratable dry formulations, the concentration of the therapeutants can vary widely. For use in this invention, it is contemplated that the amount of therapeutant will fall in the range of the recognized and recommended dosage equivalents derived from orally dosed and water treatments for diseases of fishes.

In general, the minimum concentrations of therapeutants in the hydrated gel formulations must be equivalent to the recognized Minimum Inhibitory Concentration (MIC) of each therapeutant used in a given formulation. For hydratable dry formulations, the minimum therapeutants' concentrations must be such that the concentrations after hydration are equal to or greater than the recognized MICs of each therapeutants used in a given formulation.

MICs have been determined for hundreds of therapeutants for thousands of disease-causing agents. These MICs are readily available in published sources, such as Stoskopf, Michael K. 1993. *Fish Medicine*, W. B. Saunders, Philadelphia, Pa., pp. 832-839; Herwig, Nelson. 1979. *Handbook of Drugs and Chemicals Used in the Treatment of Fish Diseases*, Charles C. Thomas, Publishers, Springfield, Ill.; Kuhns, John Farrell. 1981. "FISHDRUG/TXT: a computer generated bibliographic index of the drugs and chemicals used in treating fish diseases—part I", *The Journal of Aquaculture*, 2:4-18; Kuhns, John Farrell. 1981. "FISHDRUG/TXT: a computer generated bibliographic index of the drugs and chemicals used in treating fish diseases—part II", T *The Journal of Aquaculture*, 2:29-43; Kuhns, John Farrell. 1981. "FISHDRUG/TXT: a computer generated bibliographic index of the drugs and chemicals used in treating fish diseases—part III", *The Journal of Aquaculture*, 2:45-58; and Kuhns, John Farrell. 1981. "FISHDRUG/TXT: a computer generated bibliographic index of the drugs and chemicals used in treating fish diseases—part IV", *The Journal of Aquaculture*, 2:90-102, which are incorporated herein by reference.

Preferred concentrations of antimicrobial therapeutants useful in the formulations of topical medicants of this invention may fall within generally accepted ranges. By way of example rather than limitation, representative amounts include 8-Quinolinol present in a concentration from 0.021 mmol/L to 0.62 mmol/L, Acriflavine present in a concentration from 1 mg/mL to 5 mg/mL, Chloramphenicol present in a concentration from 25 mg/mL to 100 mg/mL, Copper (II) Sulfate Pentahydrate present in a concentration of 0.3 ppm to 0.78 ppt, Kanamycin present in a concentration from 16 µg/mL to 100 mg/m, Malachite Green present in a concentration from 0.01 mg/mL to 1.0 mg/mL, Methylene Blue present in a concentration from 3 mg/mL to 5 mg/mL, Neomycin present in a concentration from 8 µg/mL to 660 µg/mL, Nifurpirinol present in a concentration from 0.1 mg/L to 100 mg/L, Nitrofurazone present in a concentration from 9 mg/L to 100 mg/L, Norfloxacin present in a concentration from 0.4 mg/mL to 100 mg/mL, Oxolinic Acid present in a concentration from 0.025 mg/mL to 100 mg/mL, Oxytetracycline present in a concentration from 1.56 mg/mL to 100 mg/mL, Povidone-Iodine Complex present in a concentration from 1 ppt to 10 ppt, Praziquantel present in a concentration from 0.2 mg/L to 10 mg/L, Sulfisoxazole present in a concentration from 50 μg/mL to 200 μg/mL. Mixtures of the foregoing compounds can also be utilized.

The topical medicant of a hydrophilic carrier and antimicrobial therapeutant having the characteristics as previously described may also be combined with various known adjuncts having special animal health care characteristics. Such adjunct additives may include immune boosters, antimicrobial potentiators, buffers, osmotic and tonicity regulators, preservatives, healing aids, blood clotting and astringent substances. By way of example rather than limitation, immune-boosting agents may include alkali metal vanadates such as sodium vanadate. Antimicrobial potentiators may include various chelating agents. Appropriate buffers may include sodium bicarbonate, sodium tetraborate, sodium phosphates, potassium phosphates, tris(hydroxymethyl)aminomethane or tromethamine (TRIS), and tromethamine hydrochloride. Representative osmotic and tonicity regulators include sodium chloride, potassium chloride, and calcium chloride. Examples of preservatives include parahydroxybenzoic esters and benzoates. Suitable healing aids may include vitamins. And recognized blood clotting and astringent substances include iron salts, copper salts and tannic acid.

The hydrated gel formulations of the topical medicants of this invention may be mixed in accordance with the foregoing principles and are preferably packaged in a squeeze bottle dispenser. Of course the individual animal to be treated must be evaluated and an antimicrobial therapeutant selected which is appropriate to the integument condition needing attention. If no cleansing of the wound is necessary and if the animal is aquatic, it may typically be restrained in a net out of water while the topical medicant is squeezed from its applicator container onto the integument region to be treated. The animal may then be returned to the water. If the animal is semi-aquatic, it may be necessary to slightly moisten the integument region to be treated before application of the topical medicant in order to improve the bonding of the medicant to the animal. In either event, the medicant will remain visibly apparent at the site of application for a prolonged time.

In the case of the hydratable, dry powder formulations of this invention, they can be packaged in a squeeze bottle dispenser such that the powder may be puffed from dispenser directly onto the integument region to be treated. In the case of a fish restrained in a net, either the natural skin slime or water film on the fish will be sufficient to cause the topical medicant to hydrate on contact and form a hydrated gel at the treatment site. In the case of a semi-aquatic animal, after cleansing of the wound as necessary, the site to be treated may be washed with water, or the animal may be misted with water or immersed in order to moisten the treatment site. The topical medicant may then be puffed onto the integument region to hydrate on contact and form a hydrated gel in contact with the wound, lesion or disease site.

The dry powder formulations of this invention may also be packaged in small, dose-sized packets formed from water-soluble or hydratable, perforatable film material. Such packets can be fabricated from film made from suitable water-soluble polymers, gums or colloids, including, but not limited to, polyvinyl alcohol, polyvinyl pyrrolidone (povidone), corn zein, cellulose gums such as methyl cellulose and sodium carboxymethylcellulose, polyacrylamides, and chitosan. The packets are formed and sealed with a conventional pulsed, heat-sealing machine. If made from material having low water solubility, then it may be necessary to provide perforations in the packaging film in order to hydrate the dry powder within on contact. Use of this type of application is similar to the preceding examples for gel and dry powder formulations. The integument region to be treated is cleansed as necessary and then moistened. A packet containing the dry powder medicant is placed on the wound site and sticks there as the powder within the packaging film hydrates in place.

In addition to the packets fabricated as described, both the dry powder and gel formulations of this invention can be made as a single layer film formed from water-soluble or hydratable film material of water-soluble polymers, gums or colloids, including, but not limited to, polyvinyl alcohol, polyvinyl pyrrolidone (povidone), corn zein, cellulose gums such as methyl cellulose and sodium carboxymethylcellulose, polyacrylamides, and chitosan. On a single layer of film, a hydrated gel of this invention may be applied and then dried to create a patch to be applied to the moistened integument of an animal. Alternatively, a hydratable dry powder formulation of this invention may be applied to a single layer of premoistened film and then dried, or moistened after application to the film and then dried. In either case, the film can be cut to an appropriately sized patch and then applied to the moistened integument of an animal as previously indicated.

Representative formulations of topical medicant prepared in accordance with this invention are presented in the following examples.

FORMULATION EXAMPLE 1

In the first preferred formulation, a hydrated gel product is prepared by initially mixing together povidone (polyvinylpyrrolidone), anionic polyacrylamide, and sodium carboxymethylcellulose, at a ratio of 4.17:2.68:1 by weight to form a first dry premix. Then sodium chloride, neomycin sulfate, methyl p-hydroxybenzoate, propyl p-hydroxybenzoate and the first dry premix are combined at a ratio of 0.42:0.42:0.02:0.007:1 by weight to form a second dry premix. The second dry premix is dissolved in sterilized, totally deionized water, at a temperature of 50° to 60° F., at a ratio of 0.09:1 by weight and mixed using a high-speed, high-sheer mixer. This formulation is a hydrated gel that is suitable for use on fishes, amphibians and aquatic invertebrates to treat wounds, lesions and active sites of external bacterial infections

FORMULATION EXAMPLE 2

The second preferred formulation, a hydrated gel product is prepared by initially mixing povidone and sodium chloride at a ratio of 0.42:1 by weight to form a dry premix. This dry premix is combined with didecyldimethylammonium chloride and dissolved in totally deionized water at a temperature of 50° to 60° F., using a high-speed, high-sheer mixer, at the ratio of 0.07:0.002:1 by weight. This formulation is a hydrated gel that contains the powerful disinfectant didecyldimethylammonium chloride and is suitable for treating wounds and lesions, as well as fungal, viral and bacterial infections, on the integument of fishes, amphibians, reptiles and aquatic invertebrates.

FORMULATION EXAMPLE 3

In a third preferred formulation, the dry ingredients povidone (polyvinylpyrrolidone), anionic polyacrylamide, sodium carboxymethylcellulose, sodium chloride, and neomycin sulfate are mixed together at the ratio of 0.53:0.34:

0.127:1:1 by weight. This formulation is for use as a dry-applied, topical medicant for fishes that are extremely active and are more prone to remove topically applied treatments either through vigorous swimming or by flashing or other behavior that can physically remove topically applied treatments.

FORMULATION EXAMPLE 4

In a fourth preferred formulation the same dry topical medicant of the foregoing Formulation Example 3, was prepared and then packaged in a water-soluble bag composed of polyvinyl alcohol (PVA). This bag may be perforated, through and through on both sides with a common push pin, or other suitable perforating device, to provide a grid of holes through the bag to allow the escape of trapped air in the packet and to facilitate quick hydration when applied to the animal being treated. In order the keep the packet's contents from escaping from the dry bags during shipping and handling, the packet is preferably perforated just prior to use on an animal.

FORMULATION EXAMPLE 5

In a fifth preferred formulation the same dry topical medicant of the previous Formulation Example 3 was prepared and applied to a moistened strip or sheet of film composed of polyvinyl alcohol (PVA). This treated film is then dried so that the medicant composition remains attached, and it is then cut or perforated such that suitably sized film pieces are produced that may then be applied to the animal being treated such that the medicant treated side of the film is in contact with the site being treated.

FORMULATION EXAMPLE 6

In a sixth preferred formulation, the topical medicant formulated as a hydrated gel as described in the foregoing Formulation Example 1 is applied to the a film strip or sheet of polyvinyl alcohol (PVA). The film with the applied gel is then dried so that the previously hydrated gel adheres to the film. The dried film is then cut to an appropriate size to be applied to the moistened integument of an animal with the medicant treated side of the film in contact with the site to be treated.

Representative specific treatments using the topical medicants of this invention as given in the following examples.

TREATMENT EXAMPLE 1

In one trial, an African lungfish that was suffering from a severe fin and tail rot condition on its tail was removed from its aquarium and, while being restrained in a hand net, a hydrated gel prepared with the therapeutant neomycin sulfate was squeezed from a dispenser onto the affected area of the tail and exposed vertebral column. The area of infection did not require any preliminary cleaning or debriding. After 24 hours, the infection had stopped in the area of the gel application. After one week, and only a single application, the damage to the fish's tail was starting to heal.

TREATMENT EXAMPLE 2

In a second trial, a fancy goldfish with a lesion at the rear of its dorsal fin was removed from its aquarium. The lesion was cleaned with a clean, dry paper towel, slightly moistened, and then a gel formulation with neomycin sulfate as the active drug was applied from a dropper bottle to the completely cover the lesion. The application of the gel was repeated every day for one week (7 applications), and at the end of this time the lesion was completely healed and there was no visible evidence of the lesion remaining.

TREATMENT EXAMPLE 3

In a third trial, a species of frog (White's tree frog) with a large lesion on its back was treated in a manner similar to the fishes in the previously cited trials. The lesion was debrided, and a dry powder mixture of neomycin and hydrophilic polymers was puffed onto the cleaned and moistened lesion. After application of the dry powder mixture, the frog was returned to its tank for observation. One week after the first and only application, the lesion was almost completely healed. At that point the frog was again removed from its tank, the healing lesion was again cleaned with a dry, sterile cotton-tipped swab, slightly moistened and a second application of the powder was made. At the end of another week the lesion was completely healed and little scarring was noted.

TREATMENT EXAMPLE 4

In a series of trials with common goldfish and koi, small packets of dry, powder mixture of neomycin and hydrophilic polymers, packaged in a hydratable flat-sided bag approximately 0.74"×0.75" were applied to one side of each of two goldfish. In the first attempt the packet was pressed into place on the side of the fish without any skin surface preparation. In the second attempt the side of the second fish was first prepared by gently wiping the skin slime away with a soft towel, then the packet was pressed into place as with the first fish. Similarly, two trials, using the same techniques, were performed with Japanese koi of approximately 10" standard length. In the two trials where the skin slime was not first wiped away the packets either float off upon returning the fish to the water (the goldfish) or floated off within a few seconds of releasing the fish to the water. In the trials where the skin slime was wiped away, the packet on the goldfish floated off immediately upon returning the fish to the water, and the packet on the koi only held a few seconds longer than on the koi where the skin slime was not wiped away. In a third trial with a goldfish, the packet was first perforated, through and through, with a common pushpin, so that tiny holes were created in both sides of the packet. This perforated packed was then applied to a goldfish, which was first prepared by (1) wiping away the skin slime, (2) immersion of the wiped fish into the water, (3) re-wiping the same area, (4) re-immersion of the fish, and (5) pressing and smoothing the packet into place on the prepared area on the fish's skin. In this final trial the packed adhered to the skin of the fish after releasing it to the water. After approximately 10 minutes' time the packet was appeared simply as pink-colored (due to the presence of cyanocobalamin in the dry powder mixture) patch on the side of the fish. After one-half hour the patch was still visible and intact. In these trials it became obvious that without piercing the packets before application to the fishes being treated, that air trapped in side the bags made them sufficiently buoyant that they easily lifted off the fishes' skin surface before properly adhering to the area where applied. By perforating the bags, the trapped air is readily pressed from the packets as they are applied, and any remaining air can easily escape as small bubbles after the fishes are returned to the water.

From the foregoing it will be seen that this invention is one well adapted to attain all the ends and objects hereinabove set forth, together with the other advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is understood that all matter herein set forth or shown in the accompanying drawings is to be interpreted as illustrative and not in a limiting sense.

Having thus described my invention, I claim:

1. A method of therapeutic treatment to preselected integument regions of aquatic and semi-aquatic animals, the steps of said method comprising:
   selecting an antimicrobial therapeutant appropriate to the integument condition to be treated;
   determining the Minimum Inhibitory Concentration (MIC) of said antimicrobial therapeutant for efficacious treatment of the integument condition to be treated;
   selecting a hydrophilic carrier from the group consisting of polymers, resins, gums and colloids, and mixtures thereof;
   mixing said hydrophilic carrier with at least the MIC of said antimicrobial therapeutant; and
   applying topically said mixture of hydrophilic carrier and antimicrobial therapeutant to preselected integument regions of fishes, amphibians, reptiles, and aquatic macroinvertebrates.

2. The method as in claim 1 further including the step of moistening as necessary the preselected integument regions to be treated prior to topically applying said mixture of hydrophilic carrier and antimicrobial therapeutant.

3. The method as in claim 1 further including the step of formulating said mixture of hydrophilic carrier and antimicrobial therapeutant as a water-soluble resistant, hydrated gel.

4. The method as in claim 3 further including the step of adjusting the weight relationship of said hydrophilic carrier to fall in the range of 4% to 16% by weight.

5. The method as in claim 3 further including the step of adjusting the viscosity of said gel to be equal to or greater than 2.5 millipascal-seconds.

6. The method as in claim 1 further including the step of formulating said mixture of hydrophilic carrier and antimicrobial therapeutant as a dry powder capable of hydrating on contact with moisture to form a water-soluble resistant, hydrated gel.

7. The method as in claim 6 further including the step of adjusting the weight relationship of said hydrophilic carrier to be not more than 32% by weight.

8. The method as in claim 1 further including the steps of formulating said mixture of hydrophilic carrier and antimicrobial therapeutant as a dry powder capable of hydrating on contact with moisture, and packaging said dry powder in a perforatable water-soluble packet.

9. The method as in claim 8 further including the step of fabricating said packet from material selected from the group consisting of polyvinyl alcohol, polyvinylpyrrolidone, corn zein, cellulose gums, polyacrylamides, starches and chitosan.

10. The method as in claim 1 further including the steps of bonding said mixture of hydrophilic carrier and antimicrobial therapeutant to a water-soluble film selected from the group consisting of polyvinyl alcohol, polyvinylpyrrolidone, corn zein, cellulose gums, polyacrylamides, starches and chitosan, and mixtures thereof.

11. The method as in claim 1, said first selecting step comprising selecting said antimicrobial therapeutant from the group consisting of 8-Quinolinol, Acriflavine, Amoxacillin, Bistriazole, Bronopol, Chloramphenicol, Chloroquin, Cinnamon Leaf Oil, Clove Oil, Copper Salts, Eugenol, Flubendazole, Furazolidone, Gentamycin, Gentian Violet, Griesofulvin, Imidazole, Iodine, Iron Salts, Kanamycin, Macrolides, Malachite Green, Melaleuca, Merbromin, Merthiolate, Methylene Blue, Metronidazole, Miconazole, Naladixic Acid, Neomycin, Nifurpirinol, Nitrofurazone, Norfloxacin, Oxacillin, Oxolinic Acid, Oxytetracycline, Phenoxyethanol, Povidone-Iodine, Praziquantel, Quinine, Quinolines, Streptomycin, Sulfisoxazole, Tetracycline, Tolnaftate, Trimethroprin, and mixtures thereof.

12. The method as in claim 1, said first selecting and determining steps comprising selecting said antimicrobial therapeutant from the group consisting of 8-Quinolinol present in a concentration from 0.021 mmol/L to 0.62 mmol/L, Acriflavine present in a concentration from 1 mg/mL to 5 mg/mL, Chloramphenicol present in a concentration from 25 mg/mL to 100 mg/mL, Copper (II) Sulfate Pentahydrate present in a concentration of 0.3 ppm to 0.78 ppt, Kanamycin present in a concentration from 16 µg/mL to 100 mg/in, Malachite Green present in a concentration from 0.01 mg/mL to 1.0 mg/mL, Methylene Blue present in a concentration from 3 mg/mL to 5 mg/mL, Neomycin present in a concentration from 8 µg/mL to 512 µg/mL, Nifurpirinol present in a concentration from 0.1 mg/L to 100 mg/L, Nitrofurazone present in a concentration from 9 mg/L to 100 mg/L, Norfloxacin present in a concentration from 0.4 mg/mL to 100 mg/mL, Oxolinic Acid present in a concentration from 0.025 mg/mL to 100 mg/mL, Oxytetracycline present in a concentration from 1.56 mg/mL to 100 mg/mL, Povidone-Iodine Complex present in a concentration from 1 ppt to 10 ppt, Praziquantel present in a concentration from 0.2 mg/L to 10 mg/L, Sulfisoxazole present in a concentration from 50 µg/mL to 200 µg/mL, and mixtures thereof.

13. The method as in claim 1, said second selecting step comprising selecting said hydrophilic carrier from the group consisting of Polyvinylpyrrolidone, Polyvinylalcohol, Polyethyleneglycol, Alginic Acid Derivatives, Polyacrylamide, Carboxymethylcellulose, Sodium Carboxymethylcellulose, Microcrystalline Cellulose, Methylcellulose, Hydroxypropylmethylcellulose, Hydroxyethylcellulose, Ethylhydroxyethylcellulose, Agar-agar, Arabic, Alginate, Carrageen, Gelatin, Guar, Karaya, Locust Bean, Pectin, Tragacanth, Psyllium Seed, Tapioca Starch, Sago Starch, Arrowroot Starch, Larch, Quince Seed, Furcellaran, Ghatti, Gellan Gum, Pullulan, and Curdlan, and mixtures thereof.

* * * * *